United States Patent [19]
Hoogeboom et al.

[11] Patent Number: 5,282,817
[45] Date of Patent: Feb. 1, 1994

[54] ACTUATING HANDLE FOR MULTIPURPOSE SURGICAL INSTRUMENT

[76] Inventors: Thomas J. Hoogeboom, 7544 Oak Shore South, Portage, Mich. 49002-7850; James E. Hoogeboom, 3120 Scioto Trace, Columbus, Ohio 43221

[21] Appl. No.: 941,968

[22] Filed: Sep. 8, 1992

[51] Int. Cl.⁵ .......................................... A61B 17/32
[52] U.S. Cl. .................... 606/167; 606/174; 606/205; 606/206; 606/208
[58] Field of Search ............... 128/751; 606/167, 174, 606/205, 206, 208

[56] References Cited

U.S. PATENT DOCUMENTS

| | | | |
|---|---|---|---|
| 1,519,938 | 12/1924 | Smith | 294/104 |
| 1,532,020 | 3/1925 | Angelides | 294/104 |
| 1,616,121 | 2/1927 | Gruber | 81/345 |
| 2,137,710 | 11/1938 | Anderson | 606/206 |
| 2,518,994 | 8/1950 | Miller | 604/174 |
| 2,989,334 | 6/1961 | Browne | 294/104 |
| 3,146,015 | 8/1964 | Roberge | 294/104 |
| 3,265,429 | 8/1966 | Shatt | 294/104 |
| 4,393,872 | 7/1983 | Reznick et al. | 604/151 |
| 4,662,371 | 5/1987 | Whipple et al. | 606/174 |
| 4,760,848 | 8/1988 | Hasson | 606/206 |
| 4,872,456 | 10/1989 | Hasson | 606/207 |
| 4,898,157 | 2/1990 | Messroghli et al. | 606/208 |
| 4,944,093 | 7/1990 | Falk | 606/174 |
| 4,944,741 | 7/1990 | Hasson | 604/151 |
| 5,002,554 | 3/1991 | Korber | 606/174 |
| 5,009,661 | 4/1991 | Michelson | 606/205 |
| 5,089,007 | 2/1992 | Kirsch et al. | 606/205 |
| 5,152,780 | 10/1992 | Honkanen | 606/205 |
| 5,217,464 | 6/1983 | McDonald | 606/206 |

Primary Examiner—Jerome L. Kruter
Attorney, Agent, or Firm—Price, Heneveld, Cooper, DeWitt & Litton

[57] ABSTRACT

A surgical instrument for clamping, shearing, cutting or a variety of other tasks where the instrument is comprised of an elongated tube having a moveable jaw and a fixed jaw at a distal end and a pair of opposed, cooperating actuating handles at a proximal end for operating the moveable jaw by way of a pull and push rod. The moveable jaw is normally in the open position. Because at least one of the actuating handles is resiliently flexible and the actuating handles are normally bowed outward, squeezing them together produces relative proximal displacement of the pull and push rod. This proximal movement of the rod causes the moveable jaw to move proximally and to pivot about its connection to the fixed jaw resulting in the closure of the two jaws together Preferably, the surgical instrument has a removable end piece fitted in the proximal end of the elongated tube. The end piece provides support for the rod, prevents the accumulation of debris within the elongated tube and is easily removable to allow for cleaning of the instrument.

40 Claims, 3 Drawing Sheets

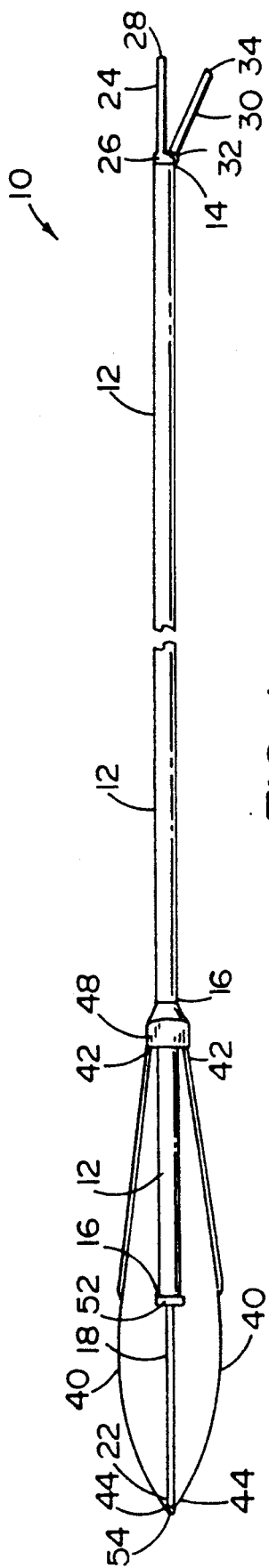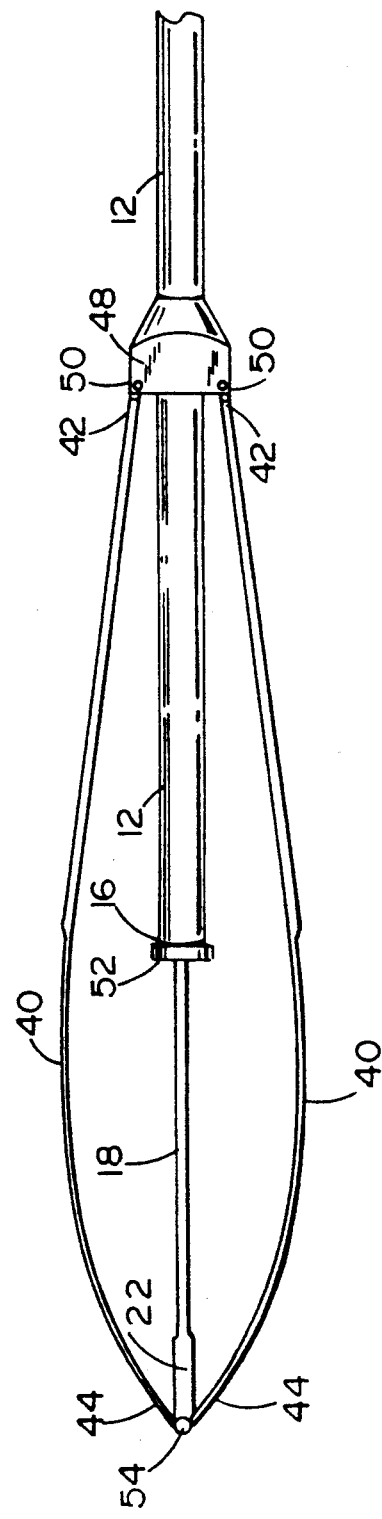

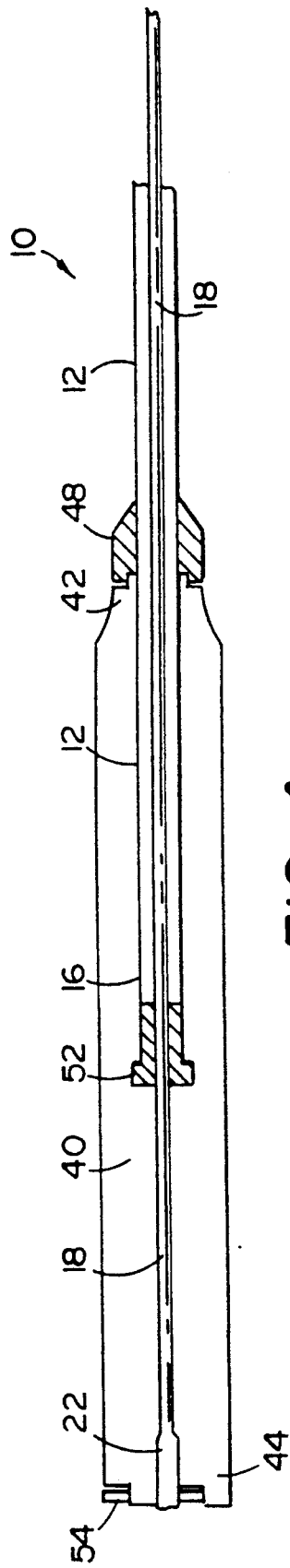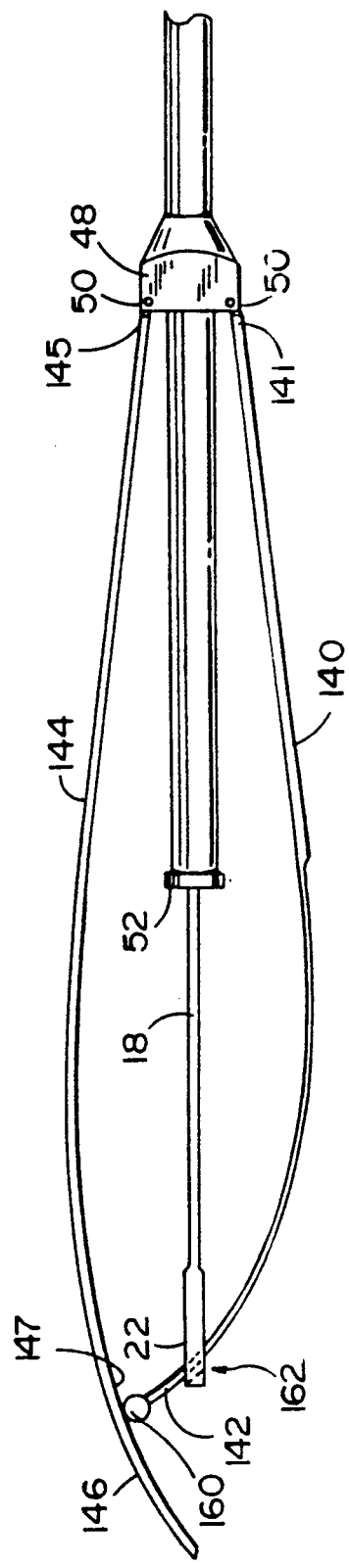

ACTUATING HANDLE FOR MULTIPURPOSE SURGICAL INSTRUMENT

BACKGROUND OF THE INVENTION

This invention relates generally to the field of surgical instruments for performing cutting, clamping, holding or shearing functions in surgical operations.

Delicate surgical operations such as microsurgery and laparoscopic surgery often require precise control over jaws or blades of instruments used in the procedure. Heretofore, few surgical instruments have been designed which provide such precise control. In order to achieve maximum control over these instruments, it is necessary to use the muscles that control motion of the fingers because they are capable physiologically of more precise control and remarkable finesse.

While U.S. Pat. Nos. 4,760,848 to Hasson and 4,898,157 to Messroghli et al. do disclose surgical instruments which exploit these more sensitive muscles, the instruments are unnecessarily complex and, thus, are relatively expensive and difficult to clean properly. Therefore, there is a need to develop surgical instruments which utilize the hand muscles capable of providing enhanced control of the instrument yet are easy to clean and are relatively inexpensive.

SUMMARY OF THE INVENTION

The present invention provides a surgical instrument which can be easily held in the hand for use in delicate surgery. The surgical instrument includes an elongated tube having a pair of opposed actuating handles, at least one of which is resiliently flexible, connected at their first ends to the tube and operably connected proximate their second ends to each other at a point spaced from the tube. A linkage rod slidably positioned within the elongated tube is pivotally connected at one end to a moveable member and is operably connected at the other end to at least said flexible actuating handle.

In operation, the lateral compression of the resiliently flexible actuating handle, which is normally bowed outward from the other handle, causes the linkage rod to move in relationship to the elongated tube which, in turn, causes the moveable member to move. Release of pressure allows the flexible handle to flex back to its original position, moving the linkage member and the moveable member back to their original positions.

The moveable member of the instrument can be adapted relative to a fixed member or another moveable member to facilitate clamping, shearing, holding, cutting or a variety of other tasks.

BRIEF DESCRIPTION OF THE DRAWINGS

FIG. 1 is a plan view of the surgical instrument of the present invention;

FIG. 2 is a plan view of the handle of the surgical instrument of the present invention;

FIG. 4 is a cross-sectional view of the handle of the surgical instrument of the present invention taken along the lines IV—IV in FIG. 2; and FIG. 5 is a plan view of the handle of an alternate embodiment of the surgical instrument of the present invention.

DETAILED DESCRIPTION OF THE PREFERRED EMBODIMENT

Figure 3:
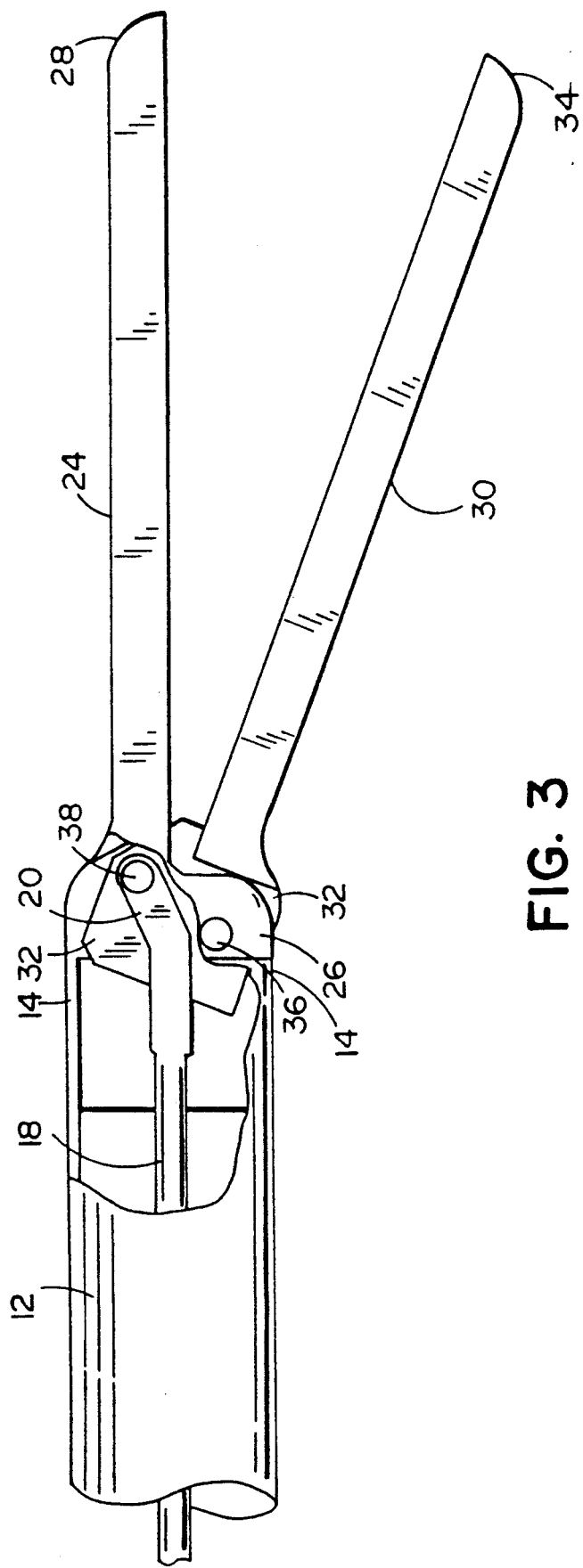
FIG. 3 is a fragmentary cross-sectional view of the jaws of the surgical instrument of the present invention.

Referring now to the drawings and the embodiments illustrated therein, in which like numerals indicate like parts throughout the several views, FIG. 1 shows a surgical instrument 10 including an elongated tube 12 having a tube first end 14 and a tube second end 16, a pair of opposing actuating members 40, a moveable jaw 30, a fixed jaw 24 and a linkage rod 18 connecting the actuating members 40 with the moveable jaw 30. The elongated tube 12, moveable jaw 30, fixed jaw 24 and the linkage rod 18 are preferably made of metal, but also could be of other appropriate materials. The opposing actuating members 40 are preferably constructed from a resilient sheet metal such as stainless steel. The gauge of the material is chosen so as to provide sufficient flexibility that plastic deformation of the tool does not occur in normal use (hence the term "resiliently flexible" hereinafter), and to provide the desired spring rate, according to the intended use of the tool. Because all of the instrument components can be made from metal, their manufacture is very straightforward and inexpensive. In addition, the instrument is easily and thoroughly cleaned and sterilized.

For purposes of description herein, the term "distal" shall refer to that portion of instrument 10 or a component thereof which is situated or moved furthest away from the body of the operator of instrument 10. The term "proximal," on the other hand, shall refer to that portion of instrument 10 or a component thereof which is situated or moved closest to the body of the operator.

As shown in FIG. 3, fixed jaw 24 has a proximal end 26 and a distal end 28 and moveable jaw 30 has a proximal end 32 and a distal end 34. Proximal end 26 of fixed jaw 24 is inserted into tube first end 14 to attach fixed jaw 24 to tube 12. Proximal end 32 of moveable jaw 30 is attached to proximal end 26 of fixed jaw 24 by a first pivot pin 36 which allows for moveable jaw 30 to pivot around the axis of first pivot pin 36.

FIGS. 1, 2, 3 and 4 illustrate that linkage rod 18, which has a rod first end 20 and a rod second end 22, is slidably positioned within tube 12. A second pivot pin 38 attaches rod first end 20 to moveable jaw 30 at a point spaced from the point of attachment of moveable jaw 30 to fixed jaw 24 by first pivot pin 36. Pivot pin 38 and pivot pin 36 are oriented so that movement of linkage rod 18 causes the movement of moveable jaw 30 about the axis of first pivot pin 36 and so that rod 18 can bias moveable jaw 30 towards the "open" position.

With reference to FIGS. 1, 2 and 4, a girdle 48 is attached to tube 12 at a point located between tube first end 14 and tube second end 16 of tube 12. Opposing 20 actuating members 40, each having a first end 42 and a second end 44, are attached to girdle 48 at the first ends 42 of actuating members 40 by connecting pins 50. Second ends 44 of actuating members 40 extend beyond tube second end 16 and are operably connected to each other by a locking pin 54 Linkage rod 18 extends proximally through tube 12 and beyond tube second end 16 through an end cap 52. Second end 22 of linkage rod 18 is operably connected to second ends 44 of actuating members 40. End cap 52 is placed in tube second end 16 to provide support for rod 18 and to prevent debris from entering the interior of tube 12.

In operation, compression of the normally outwardly bowed actuating members 40 towards each other causes the proximal movement of linkage rod 18 with respect to tube 12. The movement of linkage rod 18 is guided slidingly within the hollow portion of tube 12 by end cap 52. The proximal movement of linkage rod 18 effects the proximal movement of moveable jaw 30 which causes the rotation of moveable jaw 30 about pivot pin 36 and results in the movement of moveable jaw 30 toward fixed jaw 24.

Release of actuating members 40 causes the resiliently flexible actuating members 40 to return to their original open position. This return to the original open position causes the distal movement of linkage rod 18 with respect to tube 12 and the return of moveable jaw 30 back to the "open" position.

In an alternate embodiment as shown in FIG. 5, a flexible actuating member 140 having a first end 141 and a second end 142 and a rigid actuating member 144 having a first end 145, a second end 146 and an interior side 147 are attached to girdle 48 at first end 141 of flexible actuating member 140 and first end 145 of rigid actuating member 144 by connecting pins 50. Second end 146 of rigid actuating member 144 and second end 142 of flexible actuating member 140 each extend beyond tube second end 16 with second end 142 of flexible actuating member 140 being operably connected to rigid actuating member 144 by a roller 160 which contacts side 147. Second end 22 of linkage rod 18 is operably connected to flexible actuating member 140 near second end 142 and roller 160.

In operation, compression of the normally outwardly bowed flexible actuating member 140 toward the normally outwardly bowed rigid actuating member 144 causes roller 160 to slide proximally along interior side 147 of rigid actuating member 144. Two motions are associated with the proximal movement of flexible actuating member 140: proximal/distal and up/down. Since the only desired motion is the motion needed to move linkage rod 18 proximally and distally, the up/down motion must be dissipated. This is accomplished by fitting flexible actuating member 140 through an angled eyelet 162 located at the second end 22 of linkage rod 18. The angle at which eyelet 162 is cut in second end 22 of linkage rod 18 allows flexible actuating member 140 to slide up and down relative to linkage rod 18 while at the same time causing the proximal movement of linkage rod 18 with respect to tube 12. The movement of linkage rod 18 is guided slidingly within the hollow portion of tube 12 by end cap 52. The proximal movement of linkage rod 18 effects the proximal movement of moveable jaw 30 which causes the rotation of moveable jaw 30 about pivot pin 36 and results in the movement of moveable jaw 30 toward fixed jaw 24.

Release of flexible actuating member 140 causes it to return to its original outwardly bowed position. This return to the original open position causes flexible actuating member 140 to slide down with respect to linkage rod 18 and causes the distal movement of linkage rod 18 with respect to tube 12 and the return of moveable jaw 30 back to the "open" position.

While the foregoing describes use of the instrument in the field of surgery, the instrument may find appropriate uses in other applications requiring a small, simple jawed tool. It should be understood that moveable jaw 30 and fixed jaw 24 are just an example and that blades, needle holders, scissors, tissue forceps, smooth holding platforms, etc., could be substituted for these jaws.

It will be understood that the invention may be embodied in other specific forms without departing from the spirit or central characteristics thereof The present examples and embodiments, therefore, are to be considered in all respects as illustrative and not restrictive, and the invention is not to be limited to the details given herein and should be understood as defined by the following claims.

The embodiments of the invention in which an exclusive property or privilege is claimed are defined as follows.

1. A surgical instrument comprising:
   an elongated tubular member having first and second ends;
   a moveable working member at said first end of said tubular member;
   a pair of continuous longitudinal opposing actuating members, at least one of which is resiliently flexible, having first and second ends and being connected at their first ends to said tubular member at a point spaced from said first end of said tubular member, said actuating members extending beyond said second end of said tubular member, being operably connected to each other proximate their said second ends and said flexible actuating member being laterally compressible towards each other; and
   a linkage rod slidably positioned in said tubular member and connected to said moveable working member and extending through said tubular member and beyond said second end thereof and being operably connected to said resiliently flexible actuating member whereby lateral compression of said flexible actuating member toward the other actuating member causes said linkage rod to move said working member.

2. The surgical instrument of claim 1 in which both of said actuating members are resiliently flexible.

3. A surgical instrument in accordance with claim 2 wherein compression of said actuating members causes said linkage rod to move outwardly from said tubular member.

4. A surgical instrument in accordance with claim 3 wherein said moveable working member is a jaw for clamping.

5. A surgical instrument in accordance with claim 3 wherein said moveable working member is a blade for cutting.

6. A surgical instrument in accordance with claim 2 further comprising a removable end piece fitted in said second end of said elongated tubular member whereby said end piece provides support for said linkage rod.

7. A surgical instrument in accordance with claim 6 wherein compression of said actuating members causes said linkage rod to move outwardly from said tubular member.

8. A surgical instrument in accordance with claim 7 wherein said moveable working member is a jaw for clamping.

9. A surgical instrument in accordance with claim 7 wherein said moveable working member is a blade for cutting.

10. A surgical instrument in accordance with claim 2 wherein said actuating members are normally bowed outward from one another.

11. A surgical instrument in accordance with claim 10 wherein compression of said actuating members causes said linkage rod to move outwardly from said tubular member.

12. A surgical instrument in accordance with claim 11 wherein said moveable working member is a jaw for clamping.

13. A surgical instrument in accordance with claim 12 wherein said moveable working member is a blade for cutting.

14. A surgical instrument in accordance with claim 10 further comprising a removable end piece fitted in said second end of said elongated tubular member whereby said end piece provides support for said linkage rod.

15. A surgical instrument in accordance with claim 14 wherein compression of said actuating members causes said linkage rod to move outwardly from said tubular member.

16. A surgical instrument in accordance with claim 15 wherein said moveable working member is a jaw for clamping.

17. A surgical instrument in accordance with claim 15 wherein said moveable working member is a blade for cutting.

18. A surgical instrument in accordance with claim 1 wherein said flexible actuating member is slidably connected to said linkage rod.

19. A surgical instrument in accordance with claim 18 wherein said flexible actuating member is slidably connected to said rigid actuating member.

20. A surgical instrument in accordance with claim 19 wherein compression of said flexible actuating member causes said linkage rod to move outwardly from said tubular member.

21. A surgical instrument in accordance with claim 20 wherein said working member is a jaw for clamping.

22. A surgical instrument in accordance with claim 20 wherein said moveable working member is a blade for cutting.

23. A surgical instrument in accordance with claim 1 further comprising a removable end piece fitted in said second end of said elongated tubular member whereby said end piece provides support for said linkage rod.

24. A surgical instrument in accordance with claim 23 wherein said flexible actuating member is slidably connected to said linkage rod.

25. A surgical instrument in accordance with claim 24 wherein said flexible actuating member is slidably connected to said rigid actuating member.

26. A surgical instrument in accordance with claim 25 wherein compression of said flexible actuating member causes said linkage rod to move outwardly from said tubular member.

27. A surgical instrument in accordance with claim 26 wherein said working member is a jaw for clamping.

28. A surgical instrument in accordance with claim 26 wherein said moveable working member is a blade for cutting.

29. A surgical instrument in accordance with claim 1 wherein said pair of actuating members are bowed outward from one another.

30. A surgical instrument in accordance with claim 29 wherein said flexible actuating member is slidably connected to said linkage rod.

31. A surgical instrument in accordance with claim 30 wherein said flexible actuating member is slidably connected to said rigid actuating member 32. A surgical instrument in accordance with claim 31 wherein compression of said flexible actuating member causes said linkage rod to move outwardly from said tubular member.

33. A surgical instrument in accordance with claim 32 wherein said working member is a jaw for clamping.

34. A surgical instrument in accordance with claim 32 wherein said moveable working member is a blade for cutting.

35. A surgical instrument in accordance with claim 29 further comprising a removable end piece fitted in said second end of said elongated tubular member whereby said end piece provides support for said linkage rod.

36. A surgical instrument in accordance with claim 35 wherein said flexible actuating member is slidably connected to said linkage rod.

37. A surgical instrument in accordance with claim 36 wherein said flexible actuating member is slidably connected to said rigid actuating member.

38. A surgical instrument in accordance with claim 37 wherein compression of said flexible actuating member causes said linkage rod to move outwardly from said tubular member.

39. A surgical instrument in accordance with claim 38 wherein said working member is a jaw for clamping.

40. A surgical instrument in accordance with claim 38 wherein said moveable working member is a blade for cutting.

* * * * *

UNITED STATES PATENT AND TRADEMARK OFFICE
CERTIFICATE OF CORRECTION

PATENT NO.   : 5,282,817
DATED        : February 1, 1994
INVENTOR(S)  : Thomas J. Hoogeboom et al.

It is certified that error appears in the above-indentified patent and that said Letters Patent is hereby corrected as shown below:

On the Title Page:
In the Abstract, line 14:
    After "together" insert --.--.

Column 2, line 53:
    After "Opposing" delete --20--.

Column 2, line 59:
    After "pin 54" insert --.--.

Column 3, line 68:
    After "thereof" insert --.--.

Column 6, line 18:
    After "member" insert --.--.

Signed and Sealed this

Twenty-third Day of August, 1994

Attest:

BRUCE LEHMAN

*Attesting Officer*    *Commissioner of Patents and Trademarks*